(12) United States Patent
Guala

(10) Patent No.: US 11,975,170 B2
(45) Date of Patent: May 7, 2024

(54) ROLLER CLAMP

(71) Applicant: Industrie Borla S.p.A., Turin (IT)

(72) Inventor: Gianni Guala, Turin (IT)

(73) Assignee: INDUSTRIE BORLA S.P.A., Turin (IT)

(*) Notice: Subject to any disclaimer, the term of this patent is extended or adjusted under 35 U.S.C. 154(b) by 0 days.

(21) Appl. No.: 18/045,877

(22) Filed: Oct. 12, 2022

(65) Prior Publication Data

US 2023/0128026 A1 Apr. 27, 2023

(30) Foreign Application Priority Data

Oct. 22, 2021 (IT) .................... 102021000027221

(51) Int. Cl.
*A61M 39/28* (2006.01)
*A61M 5/168* (2006.01)

(52) U.S. Cl.
CPC ........ *A61M 39/28* (2013.01); *A61M 5/16877* (2013.01)

(58) Field of Classification Search
CPC .. A61M 39/28; A61M 39/285; A61M 39/286; A61M 5/16877; A61M 5/16813; F16K 7/065
See application file for complete search history.

(56) References Cited

U.S. PATENT DOCUMENTS

| | | | |
|---|---|---|---|
| 3,918,675 A | 11/1975 | Forberg |
| 4,869,721 A | 9/1989 | Karpisek |
| 5,014,962 A | 5/1991 | Adelberg |
| 5,259,587 A | 11/1993 | D'Alessio |

FOREIGN PATENT DOCUMENTS

DE 102015202967 A1 8/2016

OTHER PUBLICATIONS

Italian Search Report and Written Opinion dated Jun. 10, 2022, 7 pp.

*Primary Examiner* — Kelsey E Cary
(74) *Attorney, Agent, or Firm* — Heslin Rothenberg Farley & Mesiti P.C.; Victor A. Cardona, Esq.

(57) ABSTRACT

Roller clamp for regulating the flow of a fluid through an elastically deformable tubing including a generally channel-shaped body whose bottom wall has a clamping surface with a longitudinal groove with a cross-section decreasingly variable from an initial end towards a terminal end. The longitudinal groove is arranged asymmetrically with respect to the lateral walls of the body.

8 Claims, 6 Drawing Sheets

SECTION C-C

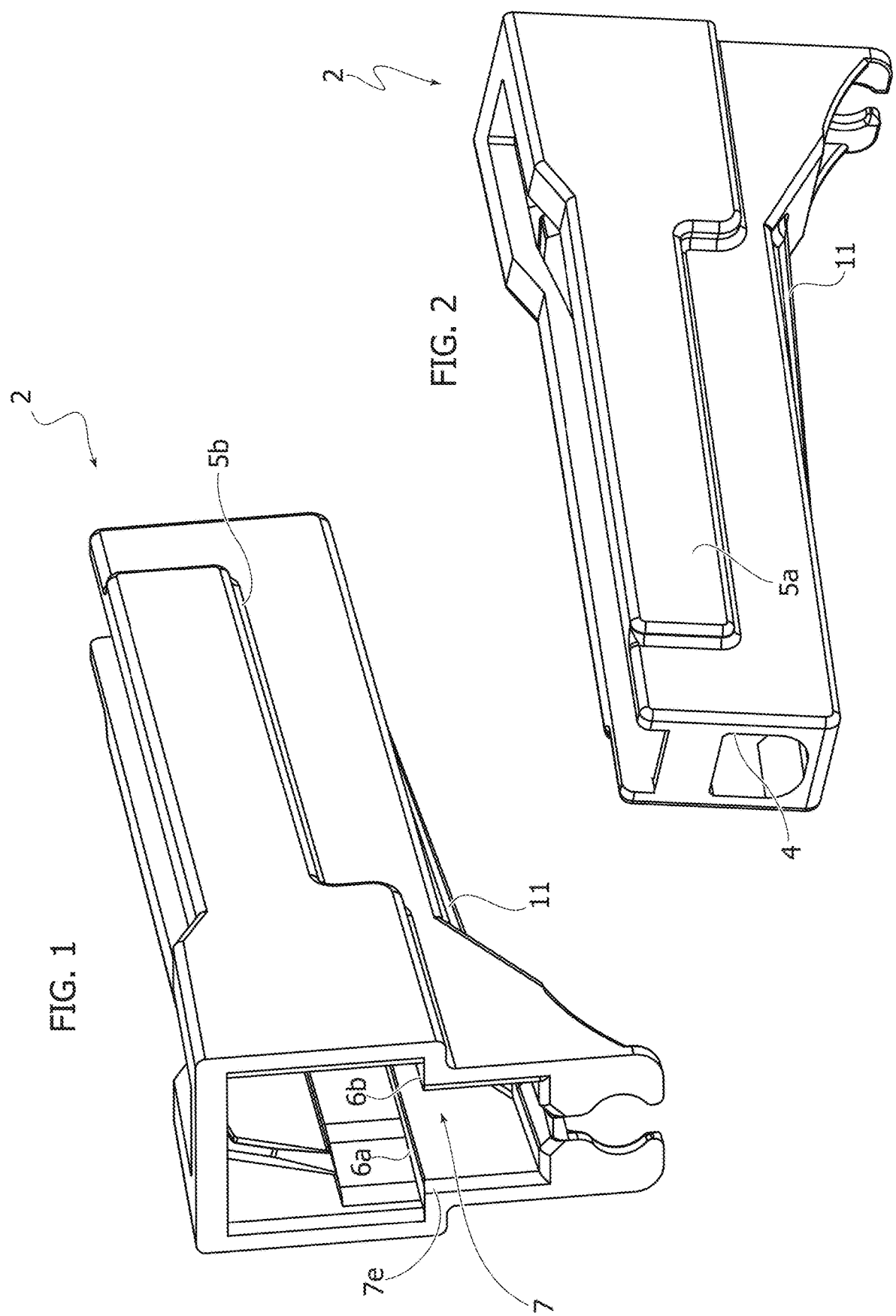

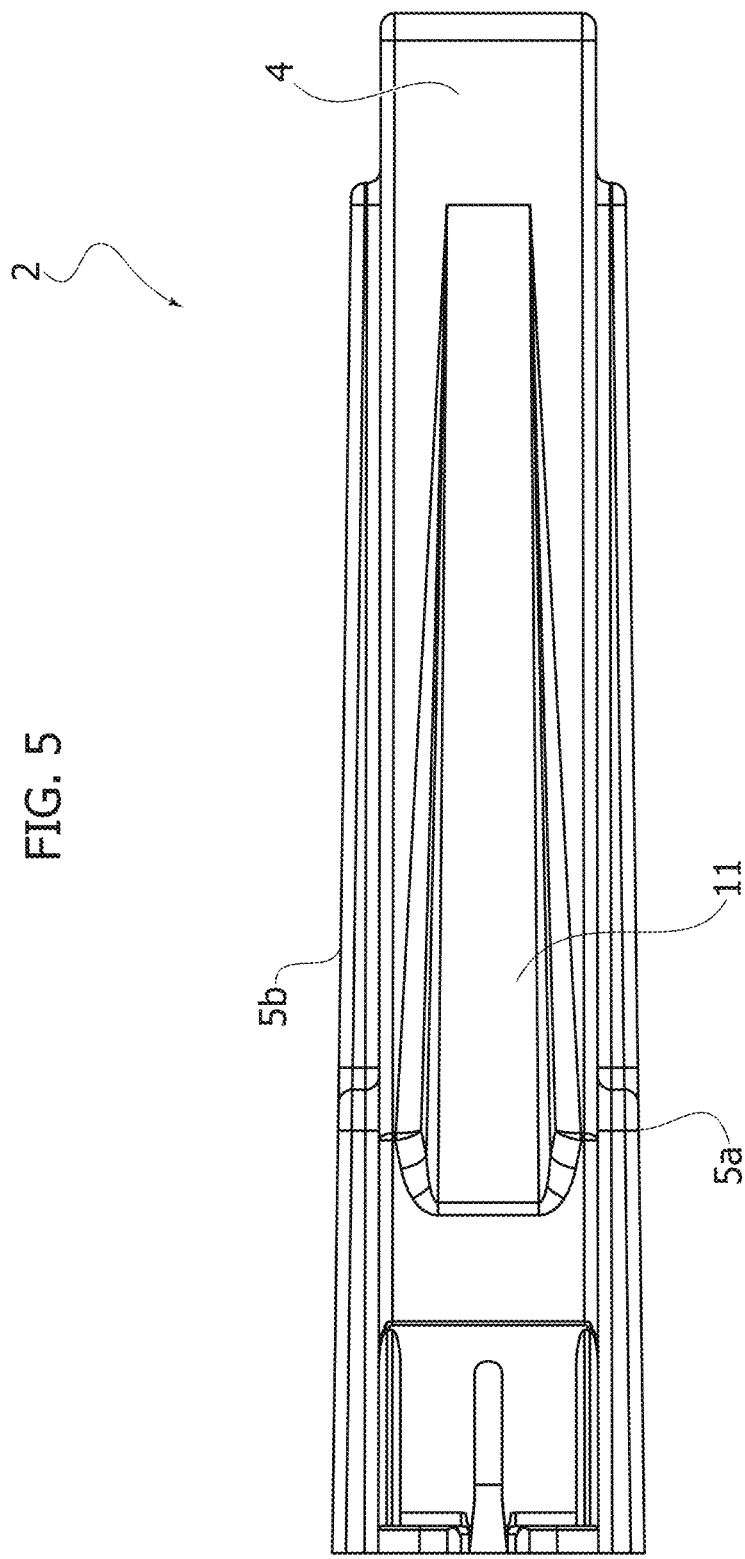

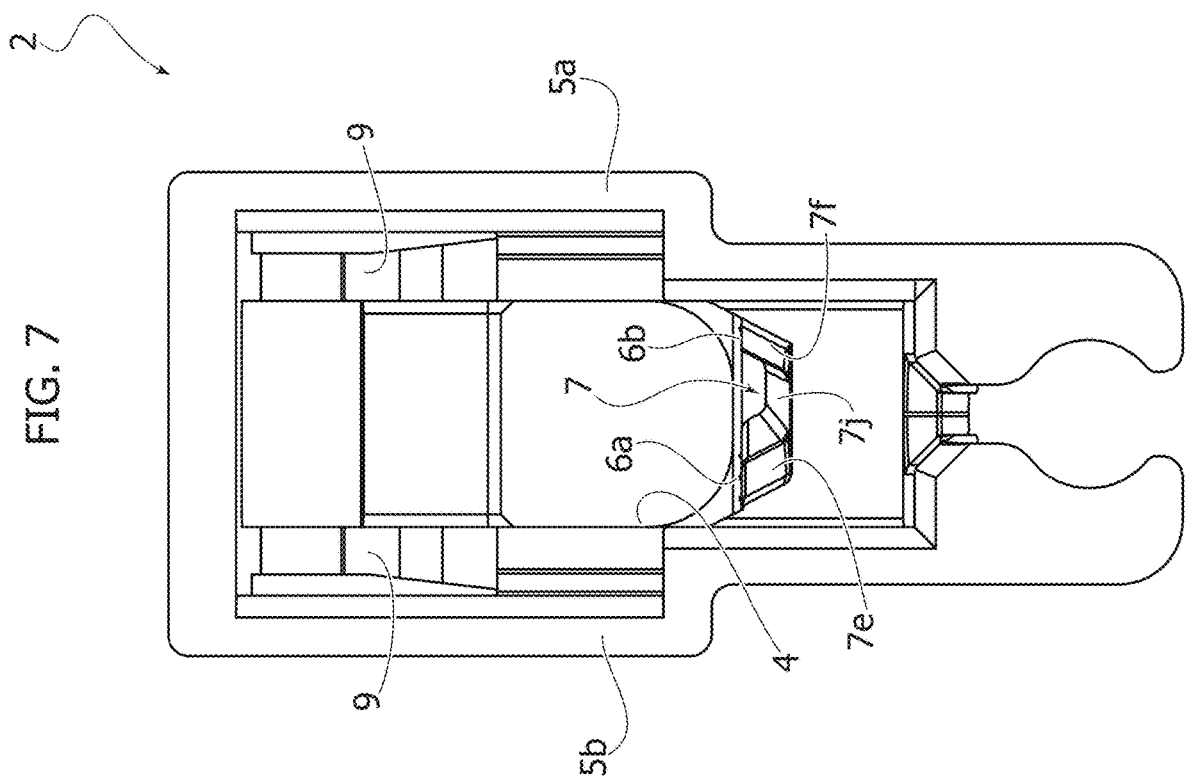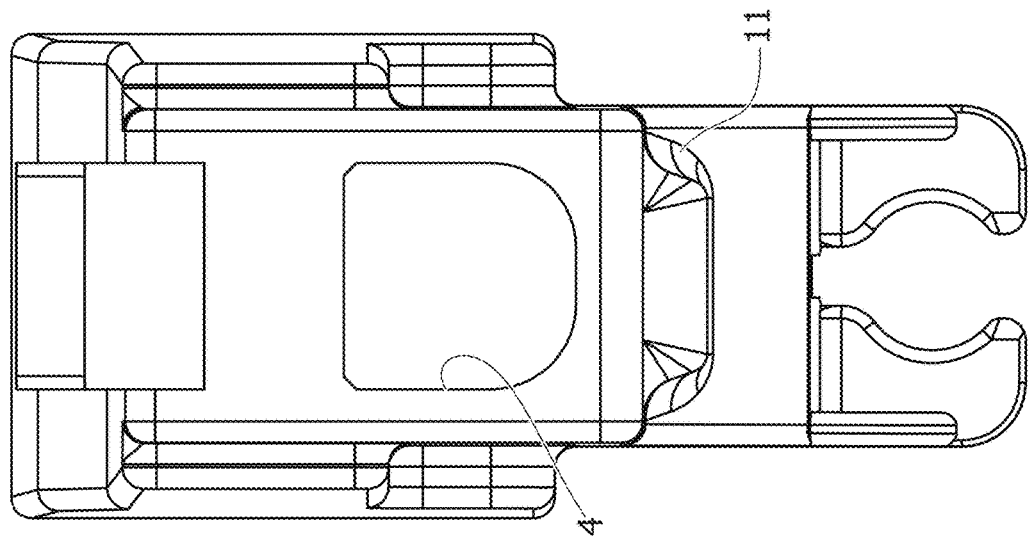

ROLLER CLAMP

CROSS REFERENCE TO RELATED APPLICATIONS

This application claims priority from Italian Patent Application No. 102021000027221 filed on Oct. 22, 2021, the entire disclosure of which is incorporated herein by reference.

FIELD OF THE INVENTION

The present invention relates to roller clamps in particular used in the medical industry for regulating the flow of a fluid through an elastically deformable tubing, for example in infusion/transfusion equipment.

More in particular, the invention relates to a roller clamp of the type comprising a generally channel-shaped body having two lateral walls and a bottom wall defining a clamping surface along at least part of which a longitudinal groove having an initial end and a terminal end is formed. The longitudinal groove has a cross-section decreasingly variable from the initial end towards the terminal end, and a roller is rotatably supported by the lateral walls of the body and it is longitudinally movable in a guided fashion on a body substantially parallelly to the clamping surface of the bottom wall for progressively clamping, in use, an elastically deformable tubing inserted through the body between the bottom wall thereof and the roller.

STATE OF THE ART

Roller clamps of the type defined above are known for example from U.S. Pat. Nos. 5,014,962 and 6,129,330, on behalf of the Applicant in question, in which the longitudinal groove formed along the clamping surface of the body of the clamp has—in cross-section—a generally V or isosceles triangle shape, that is with oblique lateral walls diverging from the bottom wall.

By using roller clamps thus made, the flow of a fluid through the elastically deformable tubing is regulated by progressively varying the longitudinal position of the roller along the clamping surface of the bottom wall of the body. The minimum or zero flow condition corresponds to the positioning of the roller at the terminal end of the longitudinal groove formed along the clamping surface of the bottom wall, while the maximum flow condition corresponds to the positioning of the roller at the initial end of the longitudinal groove. Clearly this is due to the fact that the cross-section of the tubing clamped and squeezed between the roller and the portions of the clamping surface of the bottom wall of the body, comprised between the median longitudinal groove and the lateral walls of the body, defines a narrow passage or lumen for the fluid whose width depends on the depth of the median longitudinal groove: the smaller the cross-section of the median longitudinal groove, the smaller the cross-section of the lumen, and vice versa. In other words, to positions of the roller progressively moved towards the terminal end of the longitudinal groove there corresponds a progressively narrower clamping degree of the tubing and—as a result—a progressively greater elastic deformation thereof.

In roller clamps known from the aforementioned documents, the longitudinal groove extends along a median area of the body, that is centrally with respect to the clamping surface, therefore the lumen of the flexible tubing subjected—in use—to clamping by the roller is arranged in the central area of the flexible tubing, that is between two lateral parts thereof with an equal extension whose squeezing could however not be entirely homogeneous, therefore causing possible unwanted partial through-flow, although to a limited degree. This could result into a precision limit of the flow regulation carried out by the roller clamp.

Documents U.S. Pat. Nos. 3,918,675 and 4,869,721 proposed to position the longitudinal groove asymmetrically with respect to the lateral walls of the body, in an attempt to make the operation of the clamp more precise thanks to a more controlled clamping of the tubing inserted—in use—through the body. In both of these prior art solutions, the groove has a U-shaped cross-section, that is with lateral walls orthogonal to the bottom wall.

Not even these solutions proved to be more efficient in terms of precision for regulating the flow through the tubing.

SUMMARY OF THE INVENTION

The object of the present invention is to provide a roller clamp of the type specified above that is capable of ensuring a better controlled and precise operation, and therefore more efficient.

According to the invention, this object is obtained by the characteristics mainly defined in claim 1, and secondarily in the subordinated claims.

The clamping surface of the body of the clamp is therefore asymmetric and it consists of a larger portion along one side of the longitudinal groove (the one farthest from the respective lateral wall of the body) and in a smaller portion along the other side of the longitudinal groove (the one closest to the respective lateral wall of the body). In the operation of the clamp, the squeezing of the tubing by the roller therefore occurs in an asymmetric fashion, contrary to the conventional roller clamps, in the sense that a predominant flexible tubing portion (the one corresponding to the larger clamping surface) is squeezed in a more complete and safe fashion given the larger extension thereof, while the lumen for the through-flow of the medical fluid is formed in the remaining portion with smaller extension of the flexible tubing, therefore offering a significantly improved regulation precision. Such precision is offered by the unique different conformation of the connecting transitions between the longitudinal groove and the clamping surface, one of which (the one with larger curvature radius) facilitates the deformation for the sliding of the wall of the flexible tubing, and the other (the one with smaller curvature radius) facilitates full closure by squeezing the tubing.

BRIEF DESCRIPTION OF THE DRAWINGS

Further characteristics and advantages of the invention will be more detailed from the description that follows, with reference to an embodiment shown in the attached drawings, provided purely by way of non-limiting example, wherein:

FIG. 1 is a schematic front perspective view of a roller clamp for medical use which forms an embodiment of the present invention, FIG. 2 is a rear perspective view of the body of the roller clamp, FIG. 5 is a bottom plan view of the body of the roller clamp, FIG. 6 is a front elevational view of the body of the roller clamp, FIG. 7 is a front view of the body of the roller clamp.

DETAILED DESCRIPTION OF THE INVENTION

Figure 11:
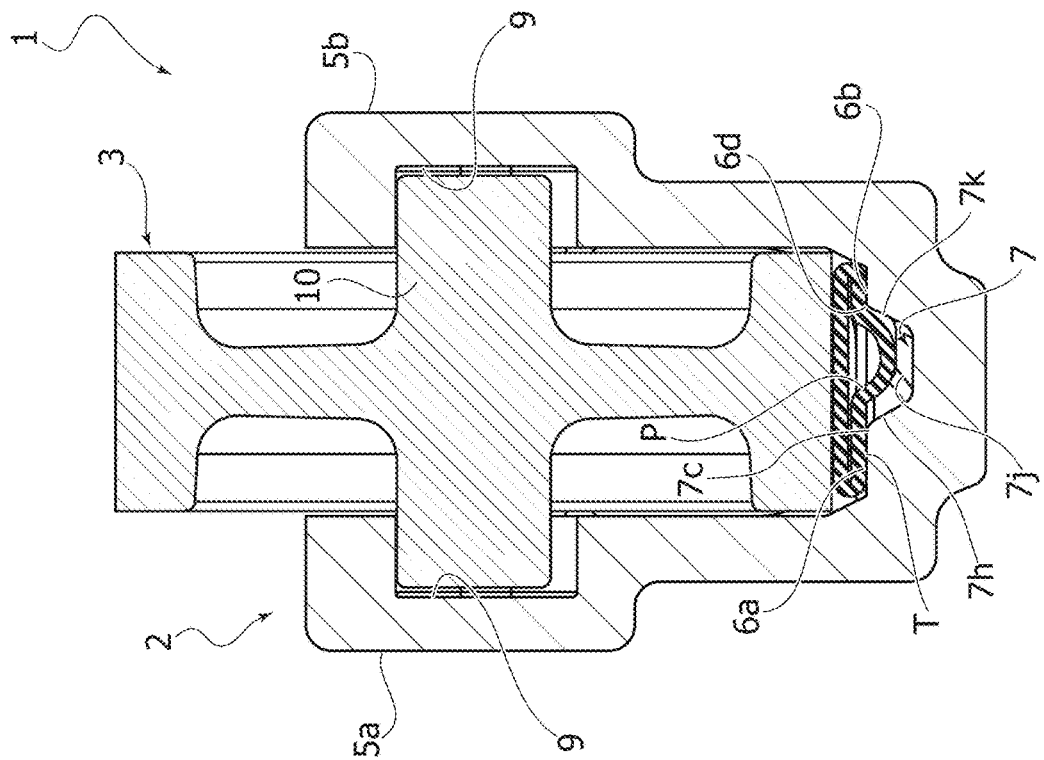
FIG. 11 is a cross-sectional view and in larger scale according to line A-A of FIG. 3 in which also the roller or the clamp and the flexible tubing are shown.
Figure 10:
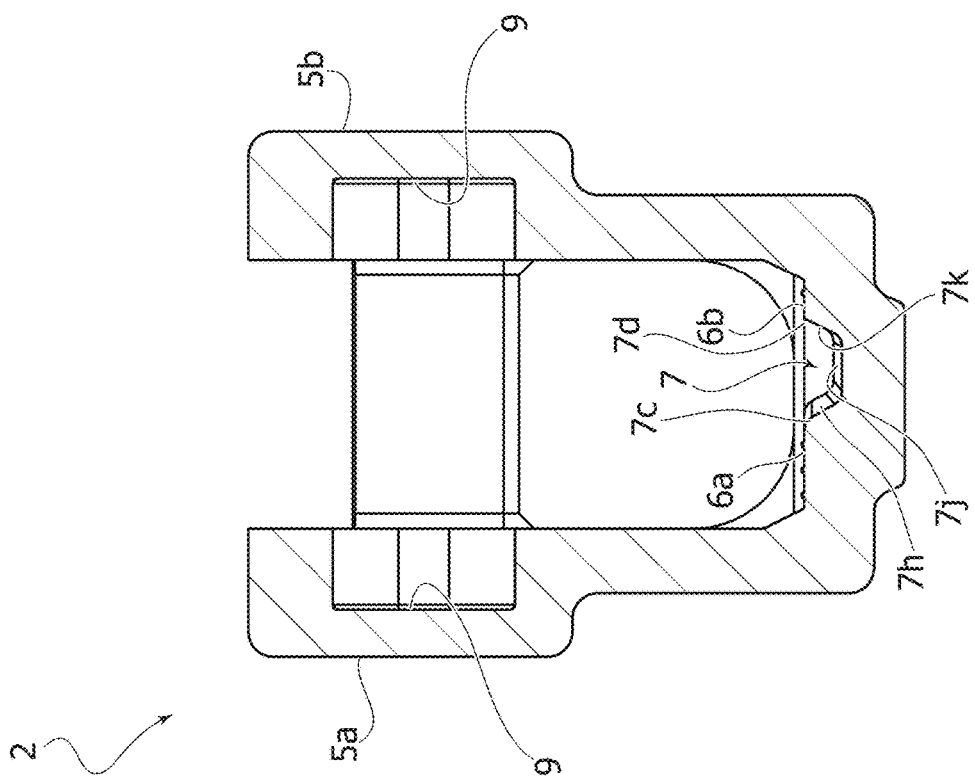

With reference to the drawings, indicated with 2 is the body of a roller clamp according to the invention, shown in its entirety with 1 in FIG. 11 and particularly designed for use in the medical field for regulating the flow of an infusion liquid, transfusion liquid or the like through an elastically deformable tubing, indicated with T still in FIG. 11.

Besides the body 2, the clamp 1 includes a roller or wheel indicated with 3 in FIG. 11, both conveniently made by moulding plastic material.

The body 2 has a general channel-like shape with a bottom wall 4 and two lateral walls respectively indicated with 5a and 5b. A lower tubular appendage 11 whose function is known, projects from the bottom wall 4.

The inner face of the bottom wall 4, that is the face facing toward the internal of the body 2, has a generally flat surface, which will be indicated hereinafter as the clamping surface of the roller clamp 1. Along most of such clamping surface there is formed a longitudinal groove 7 which identifies, along the body 2 of the clamp 1, a flow regulation region and divides the clamping surface into two clamping surface longitudinal portions indicated with 6a and 6b, one respectively adjacent to the lateral wall 5a and the other to the lateral wall 5b.

The longitudinal groove 7 formed along the clamping surface of the body 2 of the clamp has—in cross-section—a generally V or isosceles triangle shape, that is with lateral walls 7h, 7k oblique and diverging from the bottom wall 7j thereof.

The longitudinal groove 7 extends not centrally, but asymmetrically along the body 2: more particularly it is closer to the lateral wall 5b, and therefore farther from the lateral wall 5a. As a result, the clamping surface portion 6a adjacent to the lateral wall 5a has a greater width than the clamping surface portion 6b adjacent to the lateral wall 5b.

The longitudinal groove 7 has an initial end 7a and a terminal end 7b, and the cross-section thereof is decreasingly variable from the initial end 7a to the terminal end 7b. As mentioned, such cross-section of the groove 7 is substantially isosceles trapezium-shaped with smaller base, which defines the bottom wall 7j thereof, arranged on the bottom and an open larger base facing upwards.

The longitudinal edges of the longitudinal groove 7 are connected to the clamping surface portions 6a, 6b through respective curved edges 7c, 7d. More precisely, such curved edges 7c, 7d are convex and have different curvature radii: the curvature radius of the curved surface 7c which connects the lateral wall 7h with the portion 6a of the regulation surface is larger, for example in the order of 0.3 mm., than the curvature radius of the curved surface 7d which connects the lateral wall 7k with the portion 6b of the regulation surface. The curvature radius of the curved surface 7d is for example in the order of 0.05 mm.: therefore, basically such surface 7d is almost sharp-edged.

The initial end 7a of the longitudinal groove 7 is conveniently formed frontally with centring bevels 7e, 7f to facilitate the insertion of the flexible tubing T into the body 2 of the clamp 1.

Figure 3:
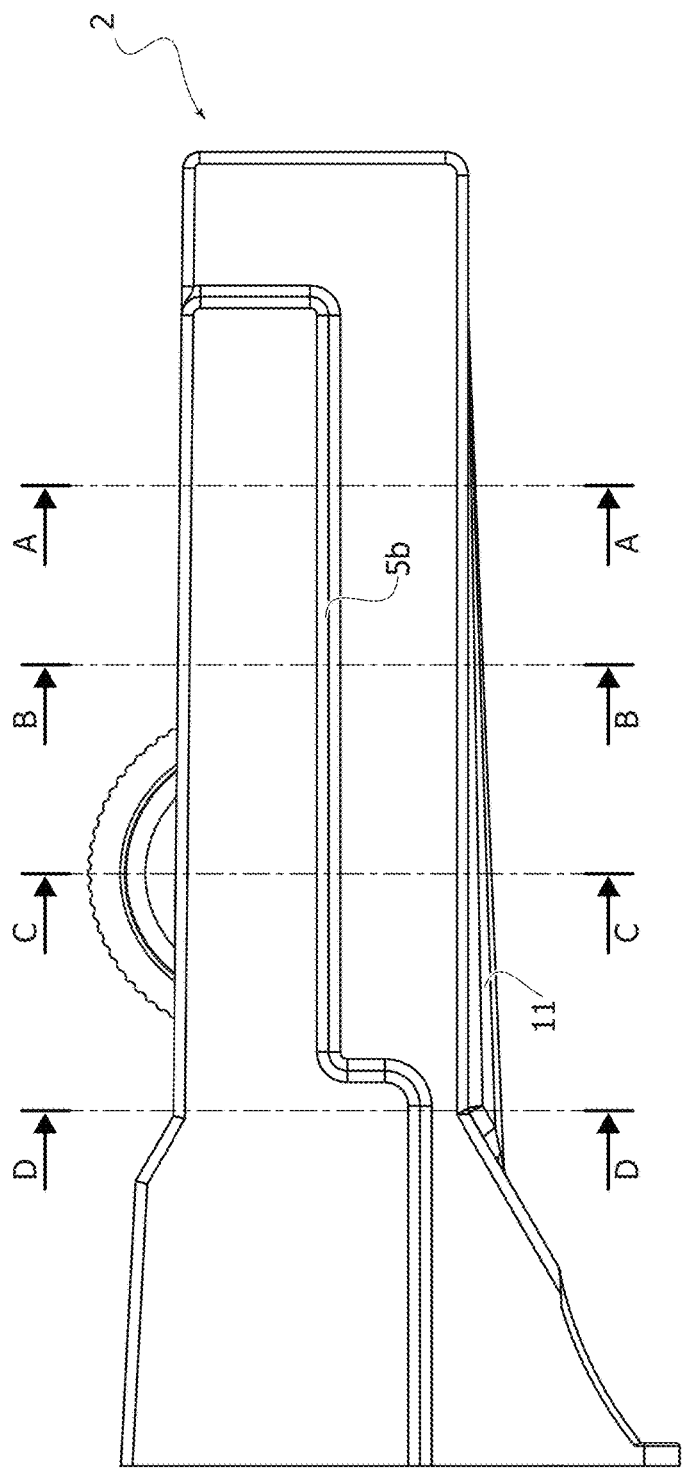
FIG. 3 is a side elevational view of the body of the roller clamp.
Figure 4:
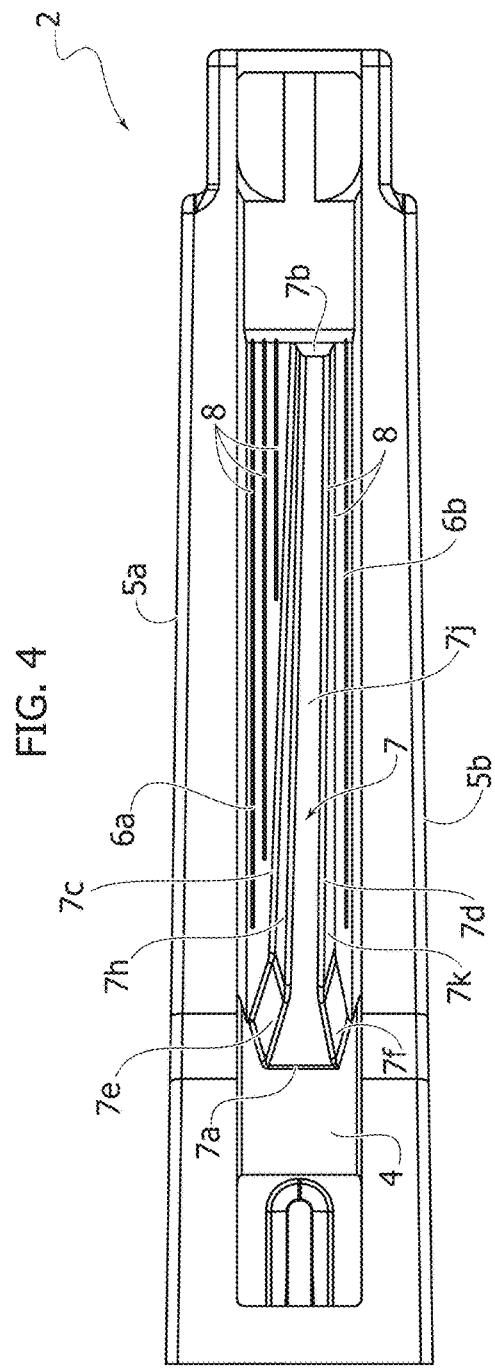
FIG. 4 is a top plan view of the body of the roller clamp.
Figure 8:
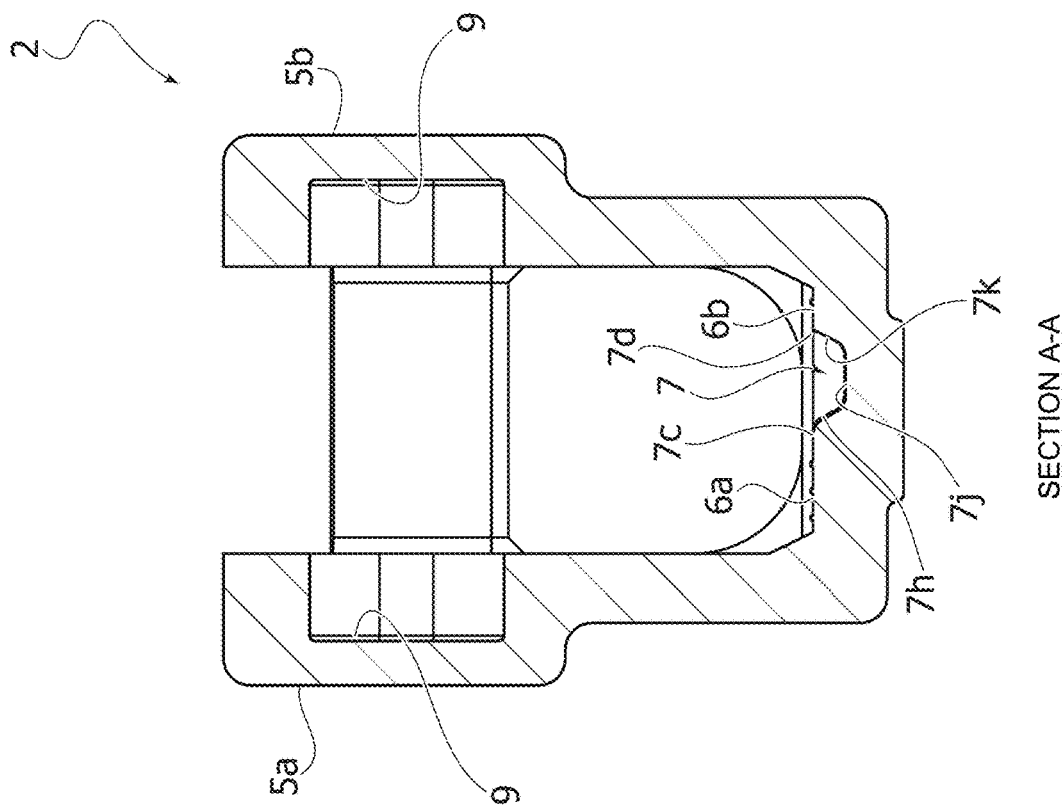
FIGS. 8, 9 and 10 are cross-sectional views respectively according to lines D-D, C-C and B-B of FIG. 3.
Figure 9:
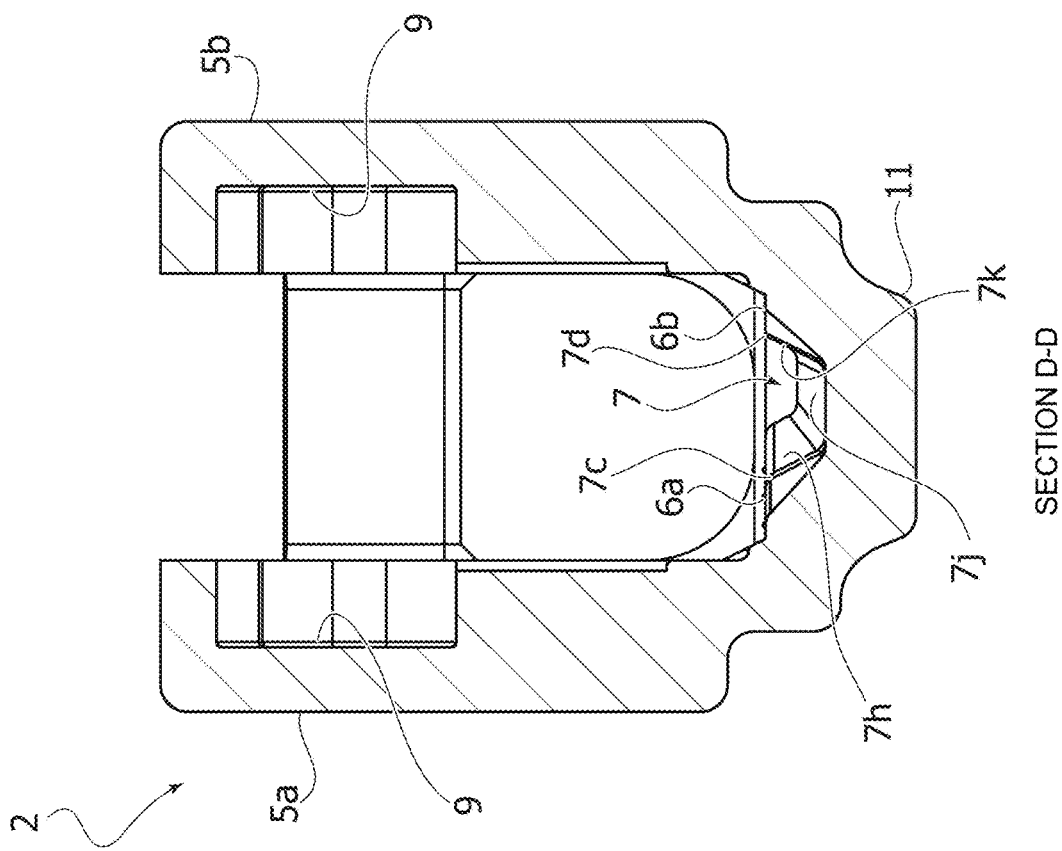

The two clamping surface portions 6a, 6b have ribs 8, that is thin grooves, which extend longitudinally beside the longitudinal groove 7 and they are conveniently arranged in an asymmetric and differentiated fashion, as better observable in FIG. 4.

Along the flow control region, the lateral walls 5a, 5b superiorly have respective inner grooves 9 which extend substantially parallelly to the clamping surface portions 6a, 6b. The two grooves 9 define respective longitudinal guides in which two axial pins 10 (FIG. 11) protruding on opposite sides of the roller 3 are engaged in a freely rotatable and slidable manner.

The roller 3 is therefore longitudinally slidable and rotatable along the guides 9 which delimit, together with the median longitudinal groove 7 and the clamping surface portions 6a, 6b, the aforementioned flow control region.

When using the elastically deformable tubing T, normally made of thermoplastic material, it is inserted into the body 2 through the front end thereof corresponding to the initial end 7a of the groove 7, between the clamping surface portions 6a, 6b and the roller 3. Should the roller 3 be positioned before the initial end 7a of the longitudinal groove 7, in the area shown in FIG. 7, the tubing T is basically undeformed, therefore no flow regulation of the liquid therein occurs. In order to regulate the flow, the roller 3 must be moved at the initial end 7a and therefore moved towards the terminal end 7b of the longitudinal groove 7, progressively in the areas shown in FIGS. 8-11. Therefore, the tubing T is progressively elastically deformed up to obtaining a substantially flat condition between the roller 3 and the clamping surface portions 6a, 6b, for example in the condition shown in FIG. 11 in which the narrow passage or lumen P whose width is directly proportional to the size of the cross-section of the longitudinal groove 7 is kept open. In other words, the size of the lumen P, and therefore the flow rate of the liquid through the tubing T, is larger given that the roller 3 is positioned at and near the initial end 7a of the median longitudinal groove 7, and it decreases progressively as the roller 3 is approached to the terminal end 7b. Should the roller 3 be further moved beyond the terminal end 7b of the longitudinal groove 7, the tubing T is squeezed to fully flattened condition, therefore the flow of the liquid is shut off.

The presence of the ribs 8 along the clamping surface portions 6a, 6b advantageously prevents the tubing T from moving laterally during the elastic deformation thereof carried out by moving the roller 3, also ensuring a more stable adaptation thereof.

Due to the fact that, according to the distinctive characteristic of the invention, the groove 7 arranged asymmetrically, has the aforementioned generally V-shaped cross-section and it is connected to the regulation surface 6a, 6b through the curved surfaces 7c, 7d with different curvatures, the tubing T is squeezed by the roller 3 against the clamping surface portions 6a, 6b even in an asymmetric and differentiated fashion, as exemplified in FIG. 11. Therefore, the predominant part thereof, that is with greater extension, corresponding to the clamping surface portion 6a, is clamped and fully closed safely and reliably, while the lumen P is located at the part with smaller extension of the tubing T corresponding to the clamping surface portion 6b. During the elastic deformation of the tubing T, the part thereof corresponding to the curved connection surface 7c with larger curvature is squeezed easily sliding on the regulation surface portion 6a, while the part corresponding to the curved connection surface 7d with smaller curvature bends and clamps against the portion 6b of the regulation surface. This allows to ensure a significantly improved precision for regulating the flow through the tubing T.

Obviously, the construction details and the embodiments may widely vary with respect to what has been described and illustrated, without departing from the scope of protection of the present invention as defined in the claims that follow.

The invention claimed is:

1. Roller clamp for regulating the flow of a fluid through an elastically deformable tubing (T), comprising:
   a generally channel-shaped body having two lateral walls and a bottom wall defining a clamping surface along at least part of which a longitudinal groove is formed having a bottom wall, lateral walls, an initial end and a terminal end and having a cross section decreasingly variable from said initial end towards said terminal end, and
   a roller rotatably supported by said lateral walls of the body and longitudinally movable in a guided fashion in said body substantially parallel to said clamping surface for clamping the elastically deformable tubing inserted through the body between said bottom wall of said body and said roller, wherein said longitudinal groove is arranged asymmetrically with respect to said lateral walls of the body,
   said lateral walls of said longitudinal groove being oblique diverging from said bottom wall of said groove, and said longitudinal groove connected to said clamping surface through curved edges having different curvature radii, the curvature radius of a curved surface arranged on a side of the longitudinal groove that is closest to a lateral wall of the lateral walls of the body being smaller than the curvature radius of a curved surface arranged on a second side of the longitudinal groove which is farthest from the other lateral wall of the body.

2. Roller clamp according to claim 1, wherein said clamping surface has ribs extending longitudinally beside said longitudinal groove.

3. Roller clamp according to claim 2, wherein said ribs are asymmetrical.

4. Roller clamp according to claim 1 wherein said initial end of the longitudinal groove is formed with centering bevels for inserting the flexible tubing into the body of the clamp.

5. Roller clamp for regulating the flow of a fluid through an elastically deformable tubing (T), comprising:
   a generally channel-shaped body having two lateral walls and a bottom wall defining a clamping surface along at least part of which a longitudinal groove is formed, the groove being substantially V-shaped and extending along a length of the clamping surface, and the groove having a bottom wall, lateral walls, an initial end and a terminal end and having a cross section decreasingly variable from said initial end towards said terminal end, and
   a roller rotatably supported by said lateral walls of the body and longitudinally movable in a guided fashion in said body substantially parallel to said clamping surface for clamping the elastically deformable tubing inserted through the body between said bottom wall of said body and said roller, wherein said longitudinal groove is arranged asymmetrically with respect to said lateral walls of the body,
   said lateral walls of said longitudinal groove being oblique diverging from said bottom wall of said groove, and said longitudinal groove connected to said clamping surface through curved edges having different curvature radii, the curvature radius of a curved surface arranged on a side of the longitudinal groove that is closest to a lateral wall of the lateral walls of the body being smaller than the curvature radius of a curved surface arranged on a second side of the longitudinal groove which is farthest from the other lateral wall of the body.

6. Roller clamp according to claim 5, wherein said clamping surface has ribs extending longitudinally beside said longitudinal groove.

7. Roller clamp according to claim 6, wherein said ribs are asymmetrical.

8. Roller clamp according to claim 5 wherein said initial end of the longitudinal groove is formed with centering bevels for inserting the flexible tubing into the body of the clamp.

* * * * *